United States Patent
Kim

(10) Patent No.: US 9,721,368 B2
(45) Date of Patent: Aug. 1, 2017

(54) METHOD FOR ELIMINATING ARTIFACT BY DETECTING FRACTURE OF THE BRAIN IN THE COMPUTED TOMOGRAPHY IMAGE AND THE COMPUTED TOMOGRAPHY APPARATUS THEREOF

(71) Applicant: Korea University Research and Business Foundation, Seoul (KR)

(72) Inventor: Dong-Joo Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 37 days.

(21) Appl. No.: 14/823,007

(22) Filed: Aug. 11, 2015

(65) Prior Publication Data

US 2016/0048957 A1    Feb. 18, 2016

(30) Foreign Application Priority Data

Aug. 14, 2014 (KR) ........................ 10-2014-0105804

(51) Int. Cl.
| | | |
|---|---|---|
| G06K 9/00 | (2006.01) | |
| G06T 11/60 | (2006.01) | |
| A61B 6/00 | (2006.01) | |
| A61B 6/03 | (2006.01) | |
| G06T 5/00 | (2006.01) | |
| G06T 7/12 | (2017.01) | |

(52) U.S. Cl.
CPC .............. *G06T 11/60* (2013.01); *A61B 6/032* (2013.01); *A61B 6/501* (2013.01); *A61B 6/505* (2013.01); *A61B 6/5258* (2013.01); *G06T 5/005* (2013.01); *G06T 7/12* (2017.01); *A61B 6/5205* (2013.01); *G06T 2207/10081* (2013.01); *G06T 2207/30008* (2013.01); *G06T 2207/30016* (2013.01); *G06T 2211/40* (2013.01)

(58) Field of Classification Search
None
See application file for complete search history.

(56) References Cited

U.S. PATENT DOCUMENTS

2004/0210135 A1* 10/2004 Hynynen ................. A61B 8/06
                                                    600/439
2006/0239554 A1* 10/2006 Sun ....................... G06T 7/0081
                                                    382/173

(Continued)

FOREIGN PATENT DOCUMENTS

JP         2005-237441 A      9/2005

*Primary Examiner* — Tahmina Ansari
(74) *Attorney, Agent, or Firm* — Pearne & Gordon LLP

(57) ABSTRACT

A method for eliminating an artifact of a computed tomography image is provided. The method includes eliminating a machine artifact from a cross-sectional computed tomography scans of the brain; setting boundary points positioned on a horizontal axis and a vertical axis in the computed tomography image, from which the machine artifact has been eliminated; resetting a boundary point positioned at a boundary between the skull of the brain and the brain tissue based on the boundary points; detecting a position of a fracture of the brain in the computed tomography image, in which the boundary point has been reset, and overlaying a fracture region with a skull pixel; and eliminating an artifact from the computed tomography image, which has been overlaid with the skull pixel.

19 Claims, 20 Drawing Sheets

(56) References Cited

U.S. PATENT DOCUMENTS

| | | | | |
|---|---|---|---|---|
| 2010/0130848 A1* | 5/2010 | Lin | ......................... | A61B 5/055 |
| | | | | 600/410 |
| 2015/0078640 A1* | 3/2015 | Guo | ...................... | G06T 7/0083 |
| | | | | 382/131 |
| 2016/0048957 A1* | 2/2016 | Kim | ....................... | A61B 6/032 |
| | | | | 382/131 |
| 2016/0058408 A1* | 3/2016 | Kim | ..................... | A61B 6/5217 |
| | | | | 382/131 |

\* cited by examiner

METHOD FOR ELIMINATING ARTIFACT BY DETECTING FRACTURE OF THE BRAIN IN THE COMPUTED TOMOGRAPHY IMAGE AND THE COMPUTED TOMOGRAPHY APPARATUS THEREOF

CROSS-REFERENCE TO RELATED APPLICATION

This application claims the benefit of Korean Patent Application No. 10-2014-0105804 filed on Aug. 14, 2014, the disclosures of which are incorporated herein by reference.

TECHNICAL FIELD

The embodiments described herein pertain generally to a method for eliminating an artifact of a computed tomography image.

BACKGROUND

Globally, approximately 10 million new patients every year suffer from brain injury, which is likely to become the $3^{rd}$ leading cause of death of human beings by 2020. It is generally known that a primary injury, a direct result of the brain injury, cannot be recovered. However, some studies have reported that most cell death induced by the traumatic brain injury occurs several hours after the initial injury. A typical secondary brain injury is an ischemic injury, which accompanies an increase of the intracranial pressure (ICP) and a decrease of the cerebral perfusion pressure (CPP).

Currently, there are two major medical imaging techniques for evaluating the degree of a brain injury; computed tomography (CT) and magnetic resonance imaging (MRI). The magnetic resonance imaging has higher resolution and sensitivity and, thus, is better able to detect cerebral edema than the computed tomography. However, the magnetic resonance imaging is disadvantageous compared to the computed tomography because it requires longer image acquisition time than the computed tomography and a patient should keep a fixed posture during imaging. For these reasons, it has been reported that the high sensitivity of the magnetic resonance imaging has no significant clinical superiority over the computed tomography, especially for a patient with the traumatic brain injury who requires urgent treatment.

Especially, keeping a fixed posture during the magnetic resonance imaging would be more disadvantageous for pediatric patients. For example, pediatric patients with the brain injury are usually under sedation or general anesthesia before the magnetic resonance imaging as they should keep a fixed posture. The sedation or general anesthesia may cause complications in the heart and the respiratory organs, which may combine with the primary injury and trigger the secondary injury.

On the contrary, the computed tomography may be greatly effective to patients requiring urgent interventions, such as patients with traumatic brain injury or stroke. However, the computed tomography may have high user-dependency whereby the degree of structural abnormality is differently measured according to the observers. Accordingly, as an effort to reduce the user-dependency by standardizing diagnosis of brain injury based on the computed tomography, various classification systems have been suggested. Of those classification systems, Marshall classification that Marshall suggested in 1991 has been the most widely used. Marshall classification is based on six (6) categorizations for traumatic brain injury evaluation depending on the structural abnormalities including a volume of brain lesion, an extent of midline shift, compression of basal cistern, and a presence or absence of surgical interventions. Marshall classification is known to provide critical information on the prognosis of patients with the brain injury. However, Marshal classification still cannot overcome the user-dependency.

Accordingly, there has been a demand for developing a new paradigm for a computed tomography analysis system whereby the limits of the existing analysis system can be overcome.

In this regard, Japanese Patent Laid-open Publication No. 2005-237441 (entitled "Method and Apparatus for Supporting Diagnosis of Brain Disorder") describes a method for providing a more objective diagnosis result for a brain injury, which involves the steps of inputting a brain image of a patient, standardizing the brain image, and, then, carrying out a statistical analysis of the subject brain image by comparing it with a brain image of a normal person.

SUMMARY

In view of the foregoing, example embodiments provide a method for carrying out automated elimination of an artifact from a computed tomography image and, also, a method for conducting a quantitative analysis upon the progression of a lesion.

However, the problems sought to be solved by the present disclosure are not limited to the above description, and other problems can be clearly understood by those skilled in the art from the following description.

In accordance with an example embodiment, a method for eliminating an artifact of a computed tomography image is provided. The method includes eliminating a machine artifact from a cross-sectional computed tomography image of the brain; setting boundary points positioned on a horizontal axis and a vertical axis in the computed tomography image, from which the machine artifact has been eliminated; resetting a boundary point positioned at a boundary between the skull of the brain and the brain tissue based on the boundary points; detecting a position of a fracture of the brain in the computed tomography image, in which the boundary point has been reset, and overlaying a fracture region with a skull pixel; and eliminating an artifact from the computed tomography image, which has been overlaid with the skull pixel.

In another example embodiment, an apparatus for eliminating an artifact of a computed tomography image is provided. The apparatus includes a storage device that stores an artifact elimination application; and a processing unit that is arranged to interface with the artifact elimination application, wherein according to execution of the artifact elimination application, the processing unit eliminates a machine artifact from a cross-sectional computed tomography image of the brain, sets boundary points positioned on a horizontal axis and a vertical axis of the brain in the computed tomography image, from which the machine artifact has been eliminated, resets a boundary point positioned at a boundary between the skull of the brain and the brain tissue, detects a position of a fracture of the brain in the computed tomography image, in which the boundary point has been reset, and overlaying the fracture region with a skull pixel, and eliminating an artifact from the computed tomography image, which has been overlaid with the skull pixel.

In accordance with the example embodiments, an artifact of a computed tomography image can be eliminated automatically by using a fully automated algorithm. Accordingly, the example embodiments have an effect of overcoming the limit of user-dependency of the conventional commercial apparatus for analyzing a brain computed tomography image.

In addition, unlike conventional classification systems that use one or two sheets of computed tomography images, analysis can be carried out by using computed tomography images of the whole cerebrum according to the example embodiments. Accordingly, the example embodiments have an effect of improving objectivity and clarity of diagnosis by reflecting not only diffuse axonal injury but also change of brain tissues resulting from subarachnoid hemorrhage or ischemia, beyond the limit of local diagnosis.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items

DETAILED DESCRIPTION

Figure 1:
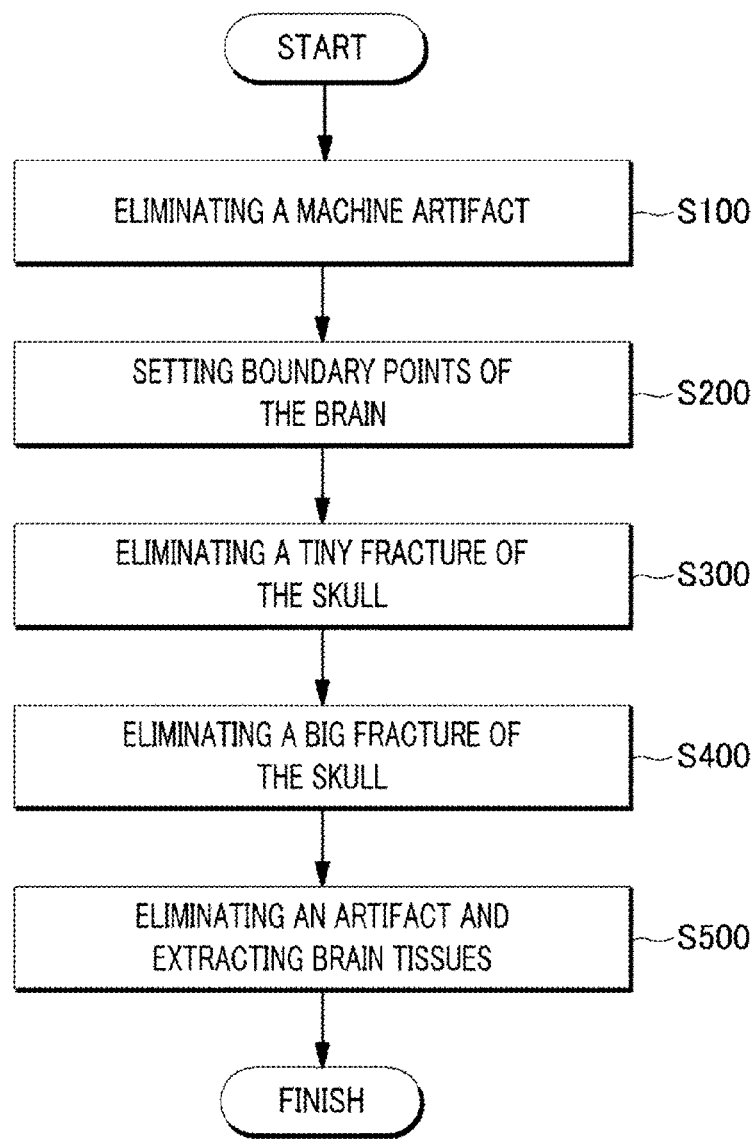
FIG. 1 is a flowchart for describing a method for eliminating an artifact of a computed tomography image in accordance with an example embodiment.

Hereinafter, example embodiments will be described in detail with reference to the accompanying drawings so that inventive concept may be readily implemented by those skilled in the art. However, it is to be noted that the present disclosure is not limited to the example embodiments but can be realized in various other ways. In the drawings, certain parts not directly relevant to the description are omitted to enhance the clarity of the drawings, and like reference numerals denote like parts throughout the whole document.

Throughout the whole document, the terms "connected to" or "coupled to" are used to designate a connection or coupling of one element to another element and include both a case where an element is "directly connected or coupled to" another element and a case where an element is "electronically connected or coupled to" another element via still another element. Further, the term "comprises or includes" and/or "comprising or including" used in the document means that one or more other components, steps, operations, and/or the existence or addition of elements are not excluded in addition to the described components, steps, operations and/or elements.

In this document, a "unit" includes a unit realized by hardware, a unit realized by software, and a unit realized by both hardware and software. In addition, one (1) unit may be realized by using two (2) or more hardware systems, and two (2) or more units may be realized by one (1) hardware system.

Hereinafter, a method for eliminating an artifact of a computed tomography image in accordance with example embodiments will be described in detail with reference to the accompanying drawings.

FIG. 1 is a flowchart for describing an artifact elimination method for a computed tomography image in accordance with an example embodiment.

Referring to FIG. 1, the artifact elimination method for a computed tomography image includes: eliminating a machine artifact (S100); setting boundary points of the brain (S200); eliminating a tiny fracture of the skull (S300); eliminating a big fracture of the skull (S400); and eliminating an artifact and extracting brain tissues (S500).

In the artifact elimination method for a computed tomography image in accordance with the example embodiment, a machine artifact present in a computed tomography image is first eliminated (s100).

In general, as a technique for acquiring cross-sectional transverse scans of body of a subject, computed tomography (CT) is carried out within a cylindrical machine which is equipped with an X-ray generator. Specifically, the X-ray generator is positioned at one side of the subject, and an X-ray detector is provided at the other side of the subject. With this configuration, aimed X-ray beams are allowed to pass through an imaging target portion of the human body at uniform intensity from multiple different directions, and a quantity of attenuated X-ray is acquired and measured by the detector on the opposite side. Based on this measurement, a computed tomography image is constructed. In this case, each pixel constituting the computed tomography image is very critically affected by the degree of X-ray absorption. The degree of X-ray absorption is called a computer tomography scale or a Hounsfield unit (HU) named after the inventor of the computer tomography. HU value of water is 0; HU value of air is −1,000; HU value of a bone having high density is +1,000; and HU values of other materials are in the range from −1,000 to +1,000 depending on the degree of X-ray attenuation. However, HU value of a machine is very close to that of a bone. In the artifact elimination method for a computer tomography image in accordance with the example embodiment, an artifact elimination based on HU value is performed at the last stage. As such, elimination of a machine artifact should be preceded.

The method of eliminating a machine artifact in accordance with the example embodiment are based on the features that there is an empty space between the machine and the brain in a computed tomography image, and the machine is located only at left, right and lower sides of the computed tomography image.

Figure 2:
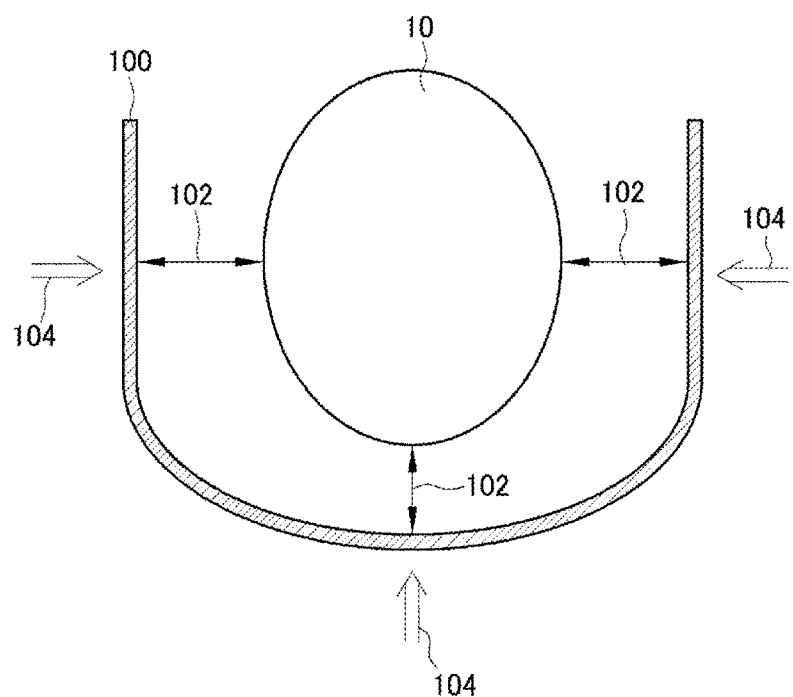
FIG. 2 is a schematic diagram for describing a method for eliminating a machine artifact, in the method for eliminating an artifact of a computed tomography image in accordance with an example embodiment.

FIG. 2 is a schematic diagram illustrating the method for eliminating a machine artifact, in the artifact elimination method for a computed tomography image in accordance with the example embodiment.

Figure 3:
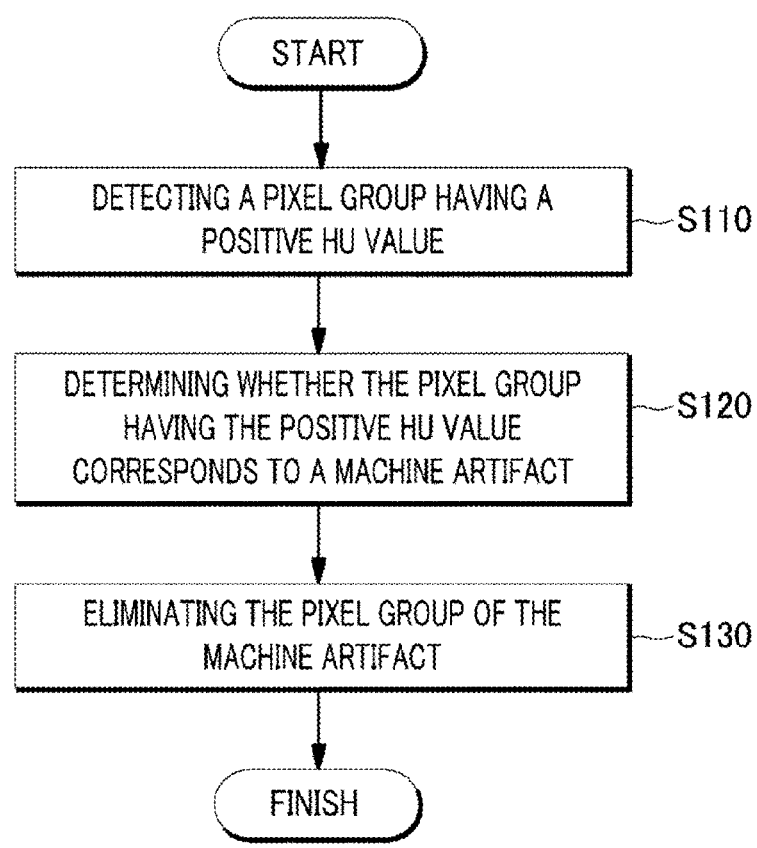
FIG. 3 is a flowchart for elaborating the process of eliminating a machine artifact in accordance with an example embodiment.

FIG. 3 is a flowchart for elaborating the process of eliminating a machine artifact in accordance with the example embodiment.

Referring to FIG. 2 and FIG. 3, the process of eliminating a machine artifact in accordance with the example embodiment includes detecting a pixel group having a positive HU value (S110); determining whether the pixel group having the positive HU value corresponds to a machine artifact (S120); and eliminating the pixel group of the machine artifact (S130).

First, at step S110 of detecting a pixel group having positive HU values, the pixel group having the positive HU values is searched by scanning the computed tomography image in the direction 104 indicated by arrows, i.e., in the direction approaching the inside of the machine from the outside of the machine.

Subsequently, at step S120 of determining whether the pixel group having the positive HU values corresponds to a machine artifact, it is determined whether or not the detected pixel group having the positive HU values corresponds to a machine artifact 100. Here, the length of a void pixel group 102 may be an important criterion for determining the machine artifact 100, and, for example, the number of void pixels may be in the range from 25 to 30.

Specifically, in the method of determining the machine artifact 100 by using the void pixel group 102 according to the example embodiment, if a series of void pixel groups 102 having negative HU values is found after the pixel group having the positive HU values is detected, that pixel group having the positive HU values is determined to be the machine artifact 100.

Alternatively, assume that a computed tomography image, in which the brain 10 and the machine artifact 100 are very close to each other, is scanned in the direction 104 approaching the inside of the machine from the outside thereof. If a second pixel group having positive HU values is found after a first pixel group having positive HU values is detected, the second pixel group having the positive HU values is determined to be pixels corresponding to the brain 10, and the first pixel group is determined to be the machine artifact 100.

Next, at step S130 of eliminating the pixel group of the machine artifact, the pixel group having the positive HU values and determined to be the machine artifact 100 is eliminated.

Meanwhile, if the second pixel group having the positive HU value is not found, the machine artifact 100 may be eliminated by combining the two methods described above.

Referring back to FIG. 1, the artifact elimination method for a computed tomography image in accordance with the example embodiment includes setting boundary points of the brain after eliminating the machine artifact 100 in the computed tomography image (S200).

Figure 4:
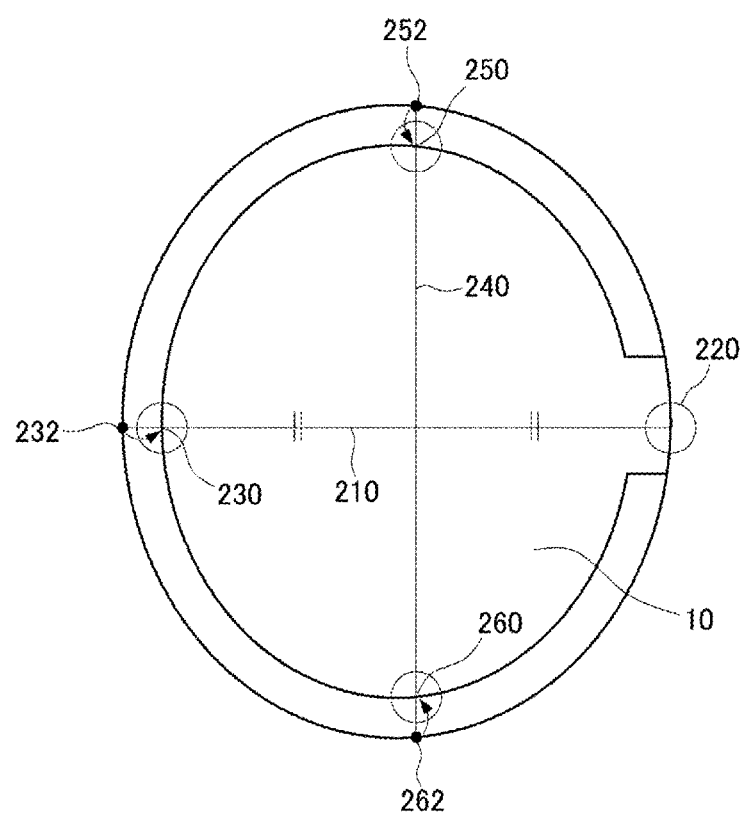
FIG. 4 is a schematic diagram for setting boundary points of the brain, in the method for eliminating an artifact of a computed tomography image in accordance with an example embodiment.

FIG. 4 is a schematic diagram for describing the way to set boundary points of the brain in the artifact elimination method for a computed tomography image in accordance with the example embodiment.

Figure 5:
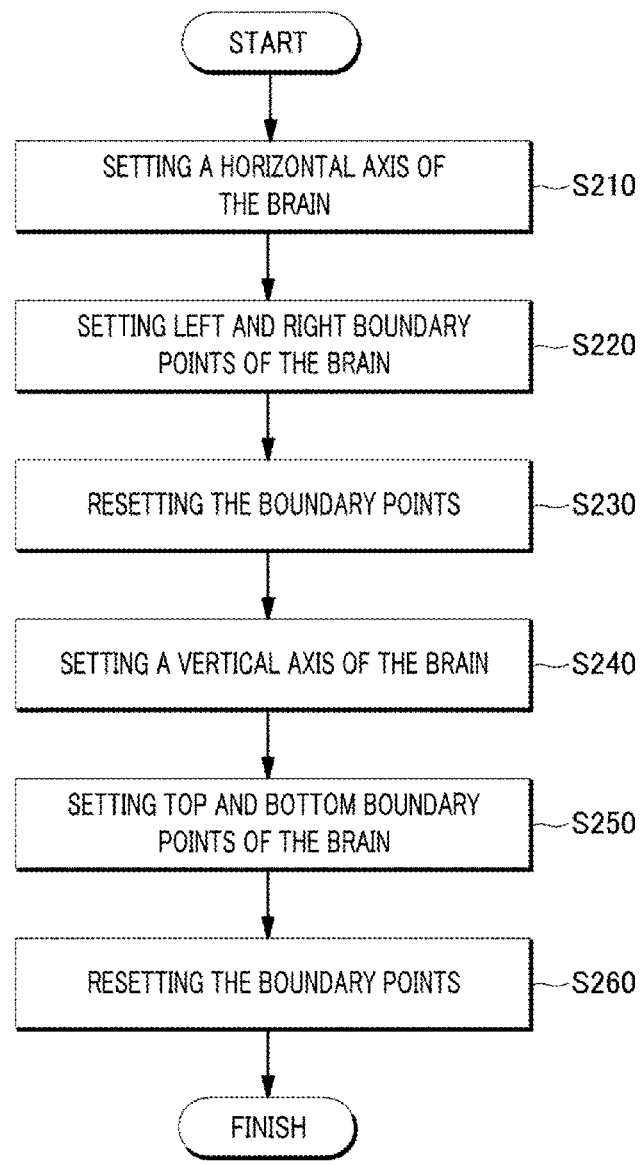
FIG. 5 is a flow chart for elaborating the process of setting the boundary points of the brain in accordance with an example embodiment.

FIG. 5 is a flowchart for elaborating the process of setting boundary points of the brain in accordance with the example embodiment.

In the artifact elimination method for a computed tomography image in accordance with the example embodiment, the length and the width of the brain can be estimated by setting top, bottom, left and right boundary points of the brain on the computed tomography image, thus enabling mathematical approach. In addition, the brain can be divided into quadrants by using the top, bottom, left and right boundary points of the brain.

Referring to FIG. 4 and FIG. 5, the step S200 of setting boundary points of the brain may include setting a horizontal axis of the brain (S210); setting left and right boundary points of the brain (S220); resetting the boundary points (S230); setting a vertical axis of the brain (S240); setting boundary top and bottom boundary points of the brain (S250); and resetting the boundary points (S260).

First, at step S210 of setting a horizontal axis of the brain, a row with the largest number of pixels having positive HU values is detected. Here, the line with the largest number of pixels having positive HU values is the one having the largest width on the brain image, and thus this line may be set as a central horizontal axis 210 of the brain.

Subsequently, left and right boundaries of a consecutive positive-number pixel group are set as a left boundary point 232 and a right boundary point 220, respectively (S220).

Thereafter, at step S230 of resetting the boundary points, the boundary points are reset, by moving the left boundary point to the boundary of the brain 10 tissue.

Figure 6:
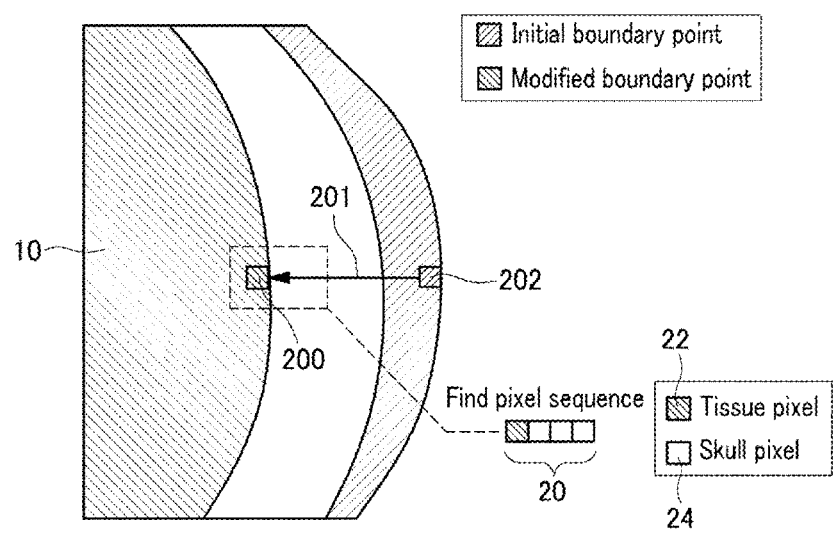
FIG. 6 is a schematic diagram for resetting the boundary points of the brain in accordance with an example embodiment.

FIG. 6 is a schematic diagram for describing the resetting of the boundary points of the brain according to the example embodiment.

Referring to FIG. 6, the initially set boundary point (the left boundary point) 202 is present outside the skull. Accordingly, it is required to reset the boundary point to be located at the boundary of the brain tissues.

At step S230 of resetting the boundary points, a pixel sequence 20 is searched by scanning the computed tomography image in a direction 201 indicated by an arrow in FIG. 6, i.e., in the direction oriented toward the center of the brain. For example, the pixel sequence 20 may be [tissue 22, skull 24, skull 24, and skull 24]. Subsequently, once the pixel sequence 20 of [tissue 22, skull 24, skull 24, and skull 24] is found, the coordinates of the tissue pixel 22 within the pixel sequence 20 are set as a modified boundary point 200. However, if such a pixel sequence 20 as [tissue 22, skull 24, skull 24 and skull 24] is not found in the scanning process, a point 200 moved from the initially set boundary point 202 in the direction 201 toward the center of the brain by 30 pixels may be set as a modified boundary point. At this time, the scanning of the pixel sequence 20 is carried out only to the center of the brain.

Meanwhile, referring to FIG. 4, in case of the right boundary point 220, skull pixel 24 may not exist because the skull is open due to the skull fracture. Accordingly, in this case, the step S200 of resetting the boundary points may be omitted.

Returning to FIG. 5, the method of setting boundary points of the brain in accordance with the example embodiment further includes setting a middle point of the horizontal axis 210 that has, as its both end points, the left boundary point 230 and the right boundary point 220 of the brain, and setting a pixel group corresponding to a column having a pixel corresponding to the middle point as a vertical axis of the brain (S240).

Subsequently, at step S250 of setting the top and bottom boundary points of the brain, an end point at the top of the vertical axis of the brain is set as a top boundary point 252, and an end point at the bottom of the vertical axis of the brain is set as a bottom boundary point 262.

Next, at step S260 of resetting the boundary points, the previously set top and bottom boundary points 252, 262 are reset to boundaries 250, 260 of the brain tissues, by the same method as described above for the resetting of the left boundary point 230.

Figure 7:
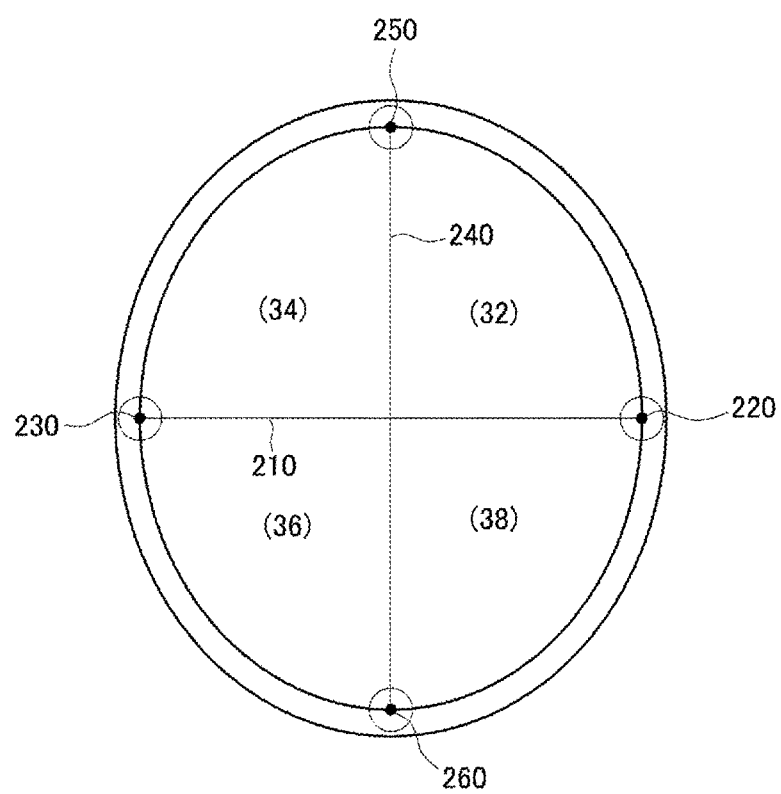
FIG. 7 illustrates dividing the brain into four split planes by using the boundary points of the brain, in the method for eliminating an artifact of a computed tomography image in accordance with an example embodiment.

FIG. 7 illustrates division of the brain image into four (4) planes by using the boundary points of the brain in the artifact elimination method for a computed tomography image in accordance with the example embodiment.

Referring to FIG. 7, in the artifact elimination method for a computed tomography image according to the example embodiment, the brain part of the computed tomography image is divided into four (4) split planes by using the above-described horizontal axis 210 and vertical axis 240 of the brain. For example, the upper right plane may be set as a first quadrant 32; the upper left plane, a second quadrant 34; the lower left plane, a third quadrant 36; and the lower right plane, a fourth quadrant 38.

Referring back to FIG. 1, in the artifact elimination method for a computed tomography image in accordance with the example embodiment, fractures present in the skull of the computed tomography image are eliminated while categorized into tiny fractures and big fractures after the boundary points of the brain are set (S300, S400). Here, as for an example way to classify fractures of the skull into tiny fractures and big fractures, a fracture which is present in a direction parallel with X or Y axis in a computed tomography image while having a length of 20 pixels or less may be regarded as a tiny fracture. Additionally, a fracture which is present in a direction having an inclination of 1 or −1 and a length of 15 pixels or less may also be regarded as a tiny fracture. Meanwhile, if the size of a fracture is larger than the aforementioned condition for being the tiny fracture, that fracture may be regarded as a big fracture. However, such criteria for the categorization of the fractures may differ by users.

Figure 8:
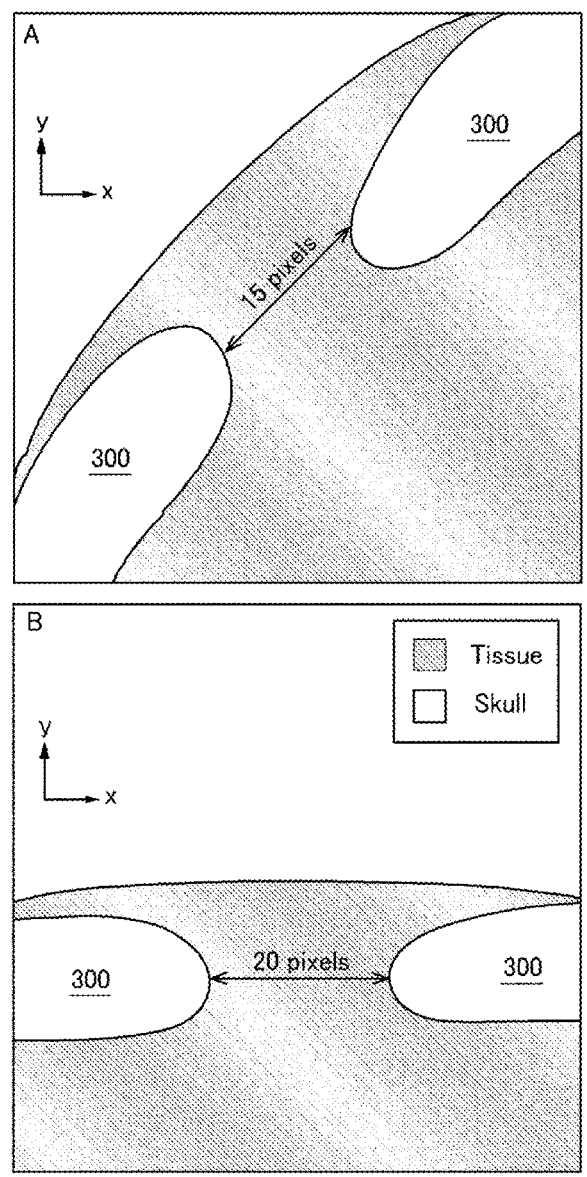
FIG. 8 is a schematic diagram showing an example of a tiny fracture in a computed tomography image in accordance with an example embodiment.

FIG. 8 is a schematic diagram illustrating examples of a tiny fracture in a computed tomography image in accordance with the example embodiment.

Figure 9:
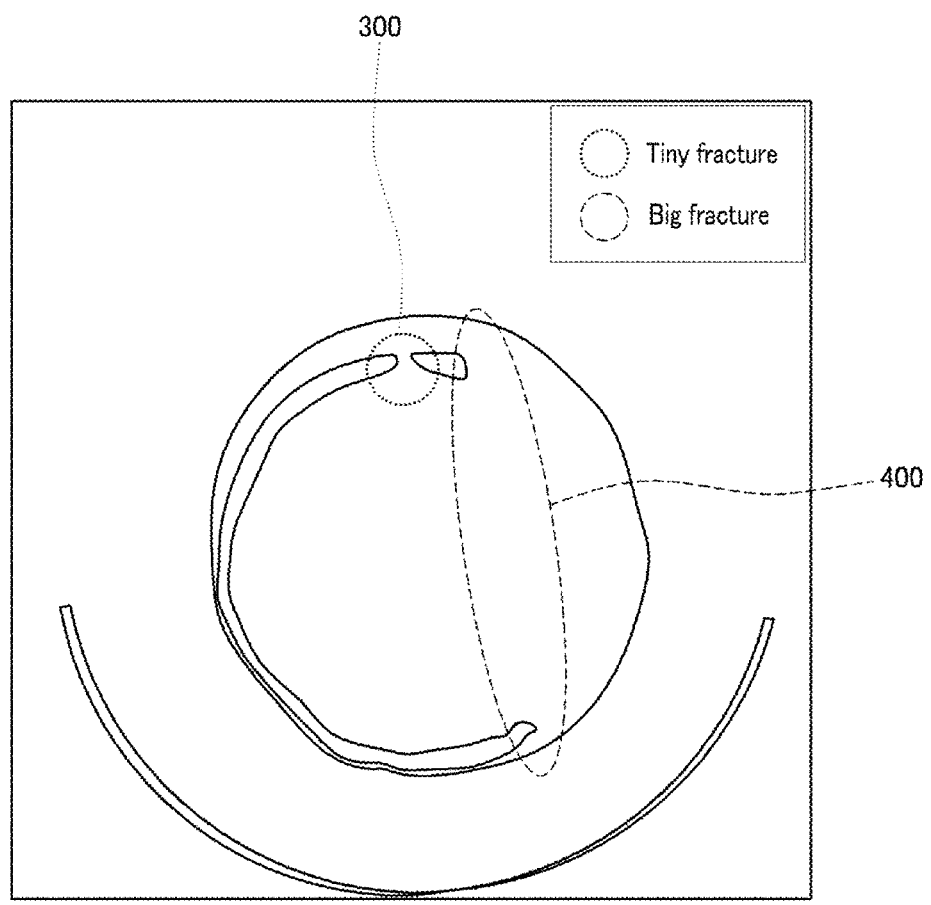
FIG. 9 is an actual image showing examples of tiny and big fractures in a computed tomography image in accordance with an example embodiment.

FIG. 9 is an actual computed tomography image showing examples of a tiny fracture and a big fracture according to the example embodiment.

Returning to FIG. 1, in the artifact elimination method for a computed tomography image in accordance with the example embodiment, a tiny fracture 300 present within the skull, which is too small to be easily observed in the computed tomography image, is first eliminated (S300).

At step S300 of eliminating a tiny fracture within the skull (S300), a pixel of a fracture regarded as a tiny fracture 300 may be replaced with a pseudo skull pixel. Here, the pseudo skull pixel means an artificial pixel having the same HU value range as that of the skull, i.e., a HU value of 80 or more. Here, when processing the tiny fracture 300, it does not matter how many fractures are processed.

Subsequently, a big fracture 400 of the brain can be eliminated by finding a starting point and an end point of the fracture of the brain and, based on this, setting a symmetrical axis (S400). If the size of the fracture is larger than the aforementioned condition for being the tiny fracture 300, or if the fracture is present across two quadrants, this fracture may be regarded as a big fracture 400. This process may be very important in evaluating a computed tomography image of a patient underwent craniotomy. Meanwhile, in the artifact elimination method for a computed tomography image in accordance with the example embodiment, it is assumed that there exists only a single big fracture in the computed tomography image.

Figure 10:
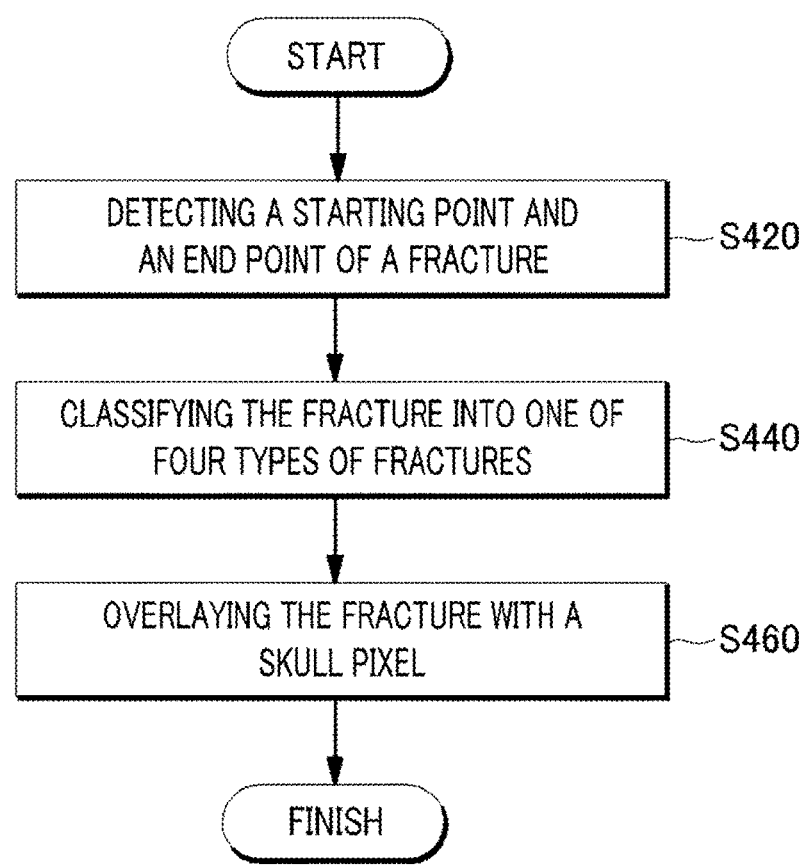
FIG. 10 is a flowchart for elaborating a process of eliminating a big fracture within the skull in a computed tomography image in accordance with an example embodiment.

FIG. 10 is a flowchart for elaborating the step of eliminating a big fracture within the skull in a computed tomography image in accordance with the example embodiment.

Referring to FIG. 10, the step S400 of eliminating a big fracture within the skull in accordance with the example embodiment includes: detecting a starting point and an end point of a big fracture (S420); categorizing the big fracture into four types of fractures (S440); and eliminating the big fracture (S460).

First, at step S400 of eliminating a big fracture within the skull in accordance with the example embodiment, a starting point and an end point of a fracture are detected first (S420).

Each pixel of a computed tomography image has a coordinate i and a coordinate j. Here, the coordinate i refers to pixels on a vertical axis, and coordinate values of the pixels increase in a downward direction on the vertical axis. Meanwhile, the coordinate j represents pixels on a horizontal axis, and coordinate values of these pixels increase in a rightward direction on the horizontal axis. However, the direction whereby the coordinate values increase or decrease may differ depending on criteria, and the present disclosure is not limited thereto.

The detection of the starting point of the fracture may start from the central axis of the brain, and skull pixels may be scanned in the direction whereby the value i increases. The scanning is performed from the top boundary point to the bottom boundary point. Here, in the artifact elimination method for a computed tomography image according to the example embodiment, a skull pixel may be used in order to find a fracture of the skull.

Figure 11:
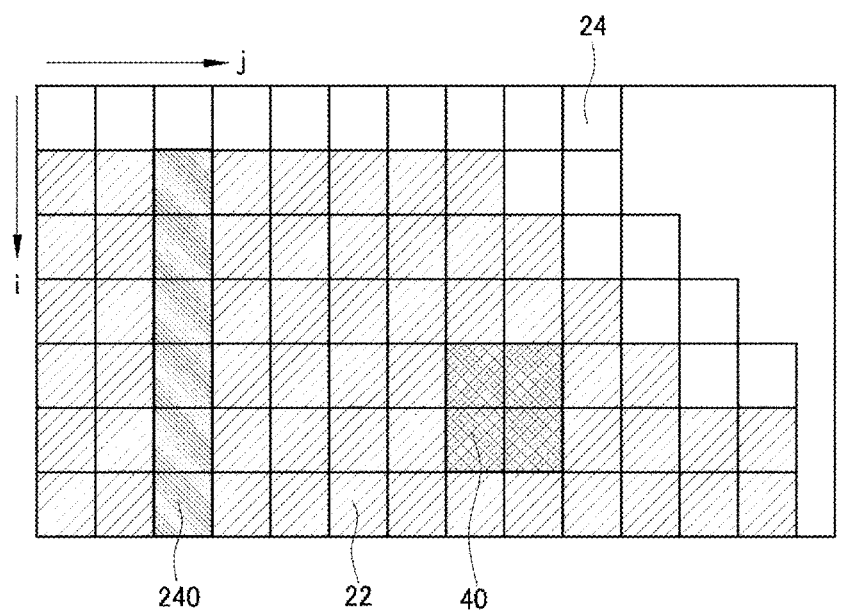
FIG. 11 shows an example case where a shunt or catheter is placed at the same height with a starting point of a fracture in the computed tomography image.

FIG. 11 is a diagram showing an example where a shunt or a catheter exists at the same height with a starting point of a fracture in a computed tomography image.

As illustrated in FIG. 11, if the skull 24 and a shunt or catheter 40 are located at the same height with a starting point of a fracture, it may be difficult to distinguish a pixel of the skull 24 and a pixel of the shunt or catheter 40, because the pixel of the skull 24 and the pixel of the shunt or catheter 40 have the same range of HU values.

Figure 12:
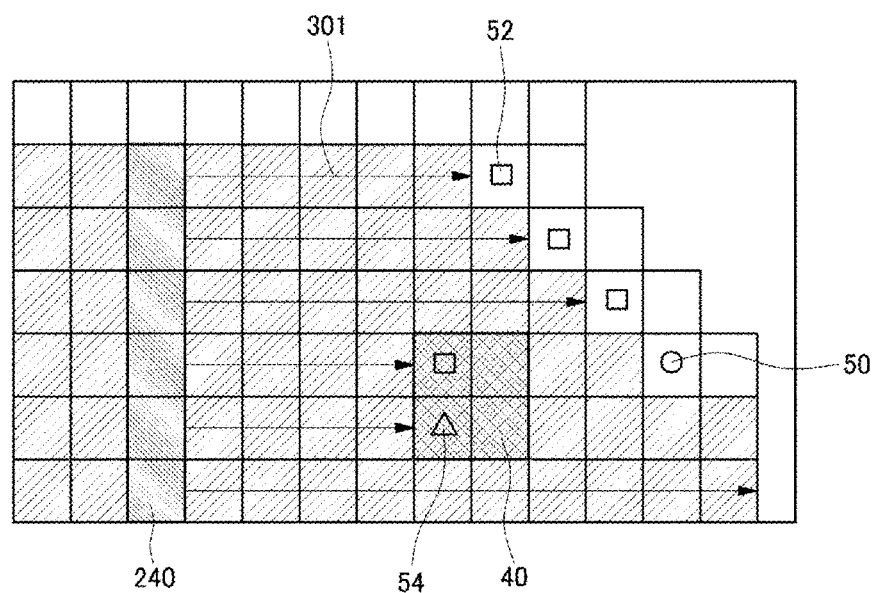
FIG. 12 illustrates an error that a starting point of a fracture is found in a shunt pixel, in a process of detecting the starting point of the fracture in a computed tomography image in accordance with an example embodiment.

FIG. 12 illustrates an error that a starting point of a fracture is set to a shunt pixel in the process of detecting the starting point of the fracture in a computed tomography image in accordance with the example embodiment.

Referring to FIG. 12, a pixel 50 indicated by a circle corresponds to a correct position of a starting point of a fracture that should have been detected, and a pixel 54 indicated by a triangle corresponds to a wrong position of the starting point of the fracture that have been detected. If the starting point of the fracture is searched by scanning started from the pixel of the central axis 240 in a direction 301 in which the value j increases while increasing only the coordinate i of the central axis, the starting point of the fracture may not be detected at the correct position of the pixel 50 indicated by the circle but may be detected at the wrong position of the pixel 54 indicated by the triangle within the shunt or catheter 40. In such cases, there is a high likelihood that the proper skull surface may not be formed and many brain tissue pixels may be lost in the process of overlaying a fracture. In view of this problem, the artifact elimination method for a computed tomography image in accordance with the example embodiment adopts an improved algorithm and, thus, can more effectively detect a starting point of a fracture.

Figure 13:
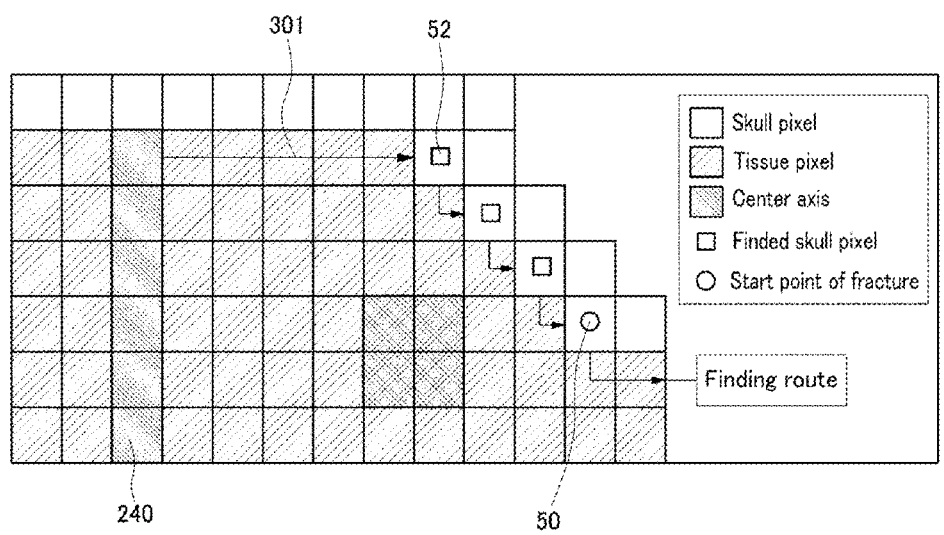
FIG. 13 illustrates a method for detecting a starting point of a big fracture, in the method for eliminating an artifact of a computed tomography image in accordance with an example embodiment.

FIG. 13 is a diagram illustrating a method for detecting a starting point of a fracture in the artifact elimination method for a computed tomography image in accordance with the example embodiment.

Referring to FIG. 13, according to the improved method for detecting a starting point of a fracture in accordance with the example embodiment, the detection may start from the pixel of the central axis 240 of the brain. For example, to detect a starting point of a fracture present on the first quadrant 32, a skull pixel 52 may be searched starting from the pixel of the central axis 240 in the direction 301 in which the value j increases. Once the skull pixel 52 is found on the first line, the target line to be scanned is shifted to a line under the current line by increasing the value i, and the detection of the skull pixel 52 is then continued on this shifted line while increasing the value j once again. At this time, the skull pixel 52 may not be found on a line with a point from which a fraction starts. Accordingly, if the value j is increased to reach the right boundary point 220 of the computed tomography image but no skull pixel 52 is found, it may be considered that a fracture of the skull has been found. Then, the coordinates of the skull pixel 50 found on the previous line may be stored as a starting point of the fracture. However, when the coordinate i exceeds the bottom boundary point 260, the detection of the starting point of the fraction is terminated, and, in this case, it is concluded that no starting point of the fraction exists. Through this algorithm, since only the pixels along the skull surface are read without needing to read all brain tissue pixels, a mistake of detecting a wrong starting point of a fracture can be avoided, and the starting point of the fracture can be accurately detected.

Now, for the detection of an end point of the fracture, since the way to detect the end point of the fracture is the same with the way to detect the starting point except that scanning is carried out in an upward direction from the bottom to the top, detailed description will be omitted.

Meanwhile, in the artifact elimination method for a computed tomography image in accordance with the example embodiment, it may be concluded that a big fraction exists if both a starting point and an end point of the fraction are found. In that case, a fracture index (fracture_flag) may be set to 1. When no fracture is found, on the other hand, the fracture index (fracture_flag) may be set to 0.

Figure 14:
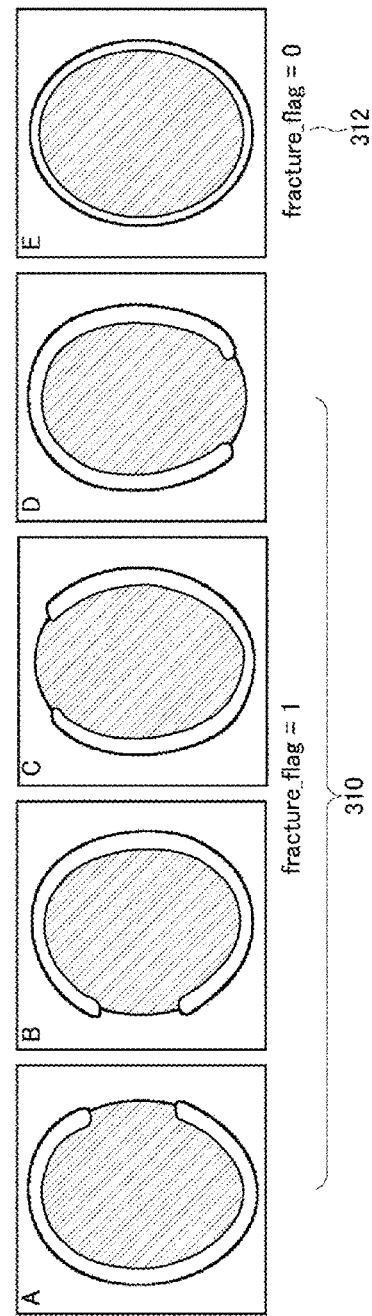
FIG. 14 illustrates an example case where a fracture index (fracture_flag) is 0 and 1, in the method for eliminating an artifact of a computed tomography image in accordance with an example embodiment.

FIG. 14 illustrates examples where fracture indexes (fracture_flag) are 0 or 1 in the artifact elimination method for a computed tomography image in accordance with the example embodiment.

Referring to FIG. 14, the fracture index of 1 means that a big fracture exists (cases 310), and the fracture index of 0 means that no fracture exists (a case 312).

Meanwhile, detection of a big fracture is carried out on all the four split planes of the brain, and the process of detecting a starting point and an end point of a fracture on each of the second quadrant 34, the third quadrant 36 and the fourth quadrant 38 is the same with the process of detecting a fracture on the first quadrant, except for scanning directions. Since the artifact elimination method according to the example embodiment is based on the assumption that only a single big fracture exists, detection of a big fracture would be terminated when the fracture index becomes 1, even though both the starting point and the end point of the fracture are found only from a single quadrant.

Next, at step S440 of categorizing the fracture into one of four types, the big fracture may be categorized as an upper, lower, left or right fracture.

Figure 15:
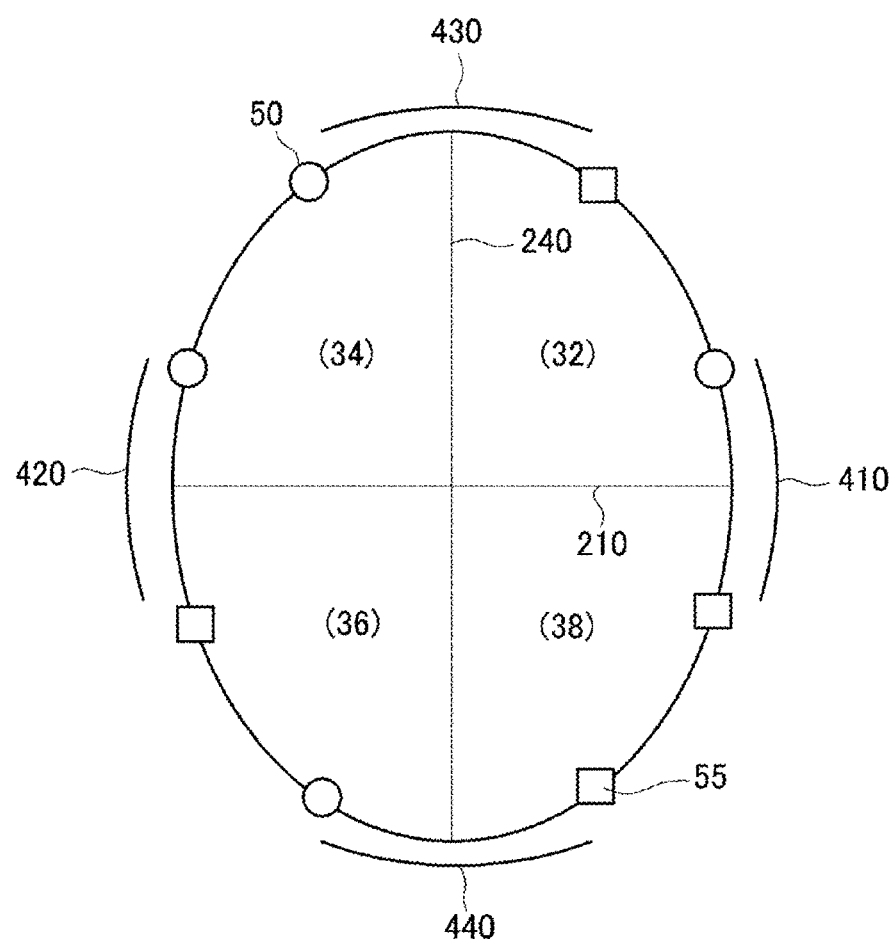
FIG. 15 shows categorizing a big fracture into one of four types of fractures based on a position thereof, in the method for eliminating an artifact of a computed tomography image in accordance with an example embodiment.

FIG. 15 is a diagram showing categorization of a fracture into one of the four types based on a position of the fracture, in the artifact elimination method for a computed tomography image in accordance with the example embodiment.

Each circle in FIG. 15 indicates a starting point 50 of a fracture, and each square represents an end point 55 of a fracture. In order to categorize a fracture, it should be determined first that which quadrant of the split planes of the brain the positions of the starting and end points belong to. Specifically, in the artifact elimination method for a computed tomography image in accordance with the example embodiment, a fracture can be sorted into one of four types based on which quadrant the starting point 50 and the end point 55 of the fracture are positioned. For example, if the starting point 50 of the fracture is present on the first quadrant 32 and the end point 55 of the fracture is present on the fourth quadrant 38, the fracture is categorized as a right fracture 410. If the starting point 50 of the fracture is present on the second quadrant 34 and the end point 55 of the fracture is present on the third quadrant 36, the fracture is categorized as a left fracture 420. If the starting point 50 of the fracture is present on the second quadrant 34 and the end point 55 of the fracture is present on the first quadrant 32, the fracture may be categorized as an upper fracture 430. If the starting point 50 of the fracture is present on the third quadrant 36 and the end point 55 of the fracture is present on the fourth quadrant 38, the fracture may be categorized as a lower fracture 440.

Next, at step S460 of eliminating a fracture, a HU value of the pixel of the found big fracture is overlaid with HU value of a skull pixel or HU value of a pseudo pixel symmetrically with respect to the closed skull surface on the opposite side. For example, if either the right fracture 410 or the left fracture 420 is found, that fracture may be matched symmetrical to a skull line of a normal skull portion on the opposite side. Subsequently, the fracture of the skull may be eliminated by replacing the HU value of the fracture portion with the HU value of the pixel of the symmetrical skull line of the normal skull portion. Here, if the right fracture 410 and the left fracture 420 are found at the same time, it is deemed that there exists the upper fracture 430 or the lower fracture 440, and the process of overlaying the pixels of the fracture with pseudo pixels may be omitted.

Subsequently, the presence of the upper or lower fracture is investigated. If either the upper fracture or the lower fracture is found, the upper fracture or the lower fracture can be eliminated by using a skull line of a normal skull portion on the opposite side. Since the method of eliminating the upper or lower fracture is the same as the method of eliminating the right or left fracture as described above, detailed description will be omitted herein. Likewise, the process of overlaying a pixel of a found fracture with a pseudo skull pixel is performed in the same way for all of the four types of fractures, except that scanning directions are different among the individual quadrants of the split planes.

Meanwhile, when overlaying a fracture with a skull pixel, in order to obtain the most similar skull shape to what would have been before the brain is opened, there may be required a process of setting a symmetrical axis with respect to the normal skull line on the opposite side without a fracture by using the starting point 50 and the end point 55 of the fracture and transferring the shape of that normal skull surface with respect to the axis of symmetry.

A process of acquiring an axis of symmetry for a right fracture and transferring a skull surface may be mathematically represented as follows.

A point, at which the right fracture starts, is defined by Mathematical Formula 1.

$$A(x_1, y_1) \quad \text{[Mathematical Formula 1]}$$

A point, at which the right fracture ends, is defined by Mathematical Formula 2.

$$B(x_2, y_2) \quad \text{[Mathematical Formula 2]}$$

Here, x and y denotes coordinates i and j of a pixel on an image.

A skull pixel on the opposite side, which is in contact with both a straight line and a brain tissue, is defined by Mathematical Formula 3.

$$C(x_3, y_2) \quad \text{[Mathematical Formula 3]}$$

A skull pixel on the opposite side, which is in contact with both a straight line and a brain tissue, is defined by Mathematical Formula 4.

$$D(x_1, y_1) \quad \text{[Mathematical Formula 4]}$$

Here, coordinates of a middle point between points A and D are represented by

Mathematical Formula 5 according to Mathematical Formulas 1 and 4.

$$\left(\frac{x_3 + x_4}{2}, y_2\right) \quad \text{[Mathematical Formula 5]}$$

In addition, coordinates of a middle point between points B and C are represented by Mathematical Formula 6 according to Mathematical Formulas 2 and 3.

$$\left(\frac{x_2 + x_3}{2}, y_2\right) \quad \text{[Mathematical Formula 6]}$$

Further, according to Mathematical Formulas 5 and 6, an equation of a straight line passing through these two middle points is defined by Mathematical Formula 7.

$$f(x) = \frac{2(y_2 - y_1)}{x_2 + x_3 - (x_1 + x_4)} x - \left(\frac{(y_2 - y_1)(x_1 + x_4)}{(x_2 + x_3) - (x_1 + x_4)} - y_1\right) \quad \text{[Mathematical Formula 7]}$$

Here, Mathematical Formula 7 is used as an axis of symmetry, based on which the shape of the skull surface is transferred. The shape of the skull surface on the opposite side without a fracture is defined by the following Mathematical Formula 8 in the form of an implicit function.

$$g(x, y_1) = 0, \; y_2 \leq y_k \leq y_1 \quad \text{[Mathematical Formula 8]}$$

Here, the shape of the skull surface to be transferred based on the axis of symmetry defined by Mathematical Formula 7 may be represented by Mathematical Formula 9 as follows.

$$g\left(\left(-x + 2\frac{y_k - N}{M}\right), y_k\right) = 0 \quad \text{[Mathematical Formula 9]}$$

Here, M may be represented by Mathematical Formula 10 below.

$$M = \frac{2(y_2 - y_1)}{x_2 + x_3 - (x_1 + x_4)} \quad \text{[Mathematical Formula 10]}$$

In addition, N is represented by Mathematical Formula 11.

$$N = -\frac{(y_2 - y_1)(x_1 + x_4)}{(x_2 + x_3) - (x_1 + x_4)} + y_1 \quad \text{[Mathematical Formula 11]}$$

In accordance with the example embodiment, once the shape of the skull surface is taken as described above, both the fracture portion and the outside of the fracture can be overlaid with pseudo skull pixels, conforming to the skull surface. Here, the reason for overlaying these portions with the skull pixels is based on the assumption that all the brain tissues are enclosed by the skull, which is the premise of the subsequent artifact eliminating process. Accordingly, the other fractures may be processed in the same way.

Figure 16:
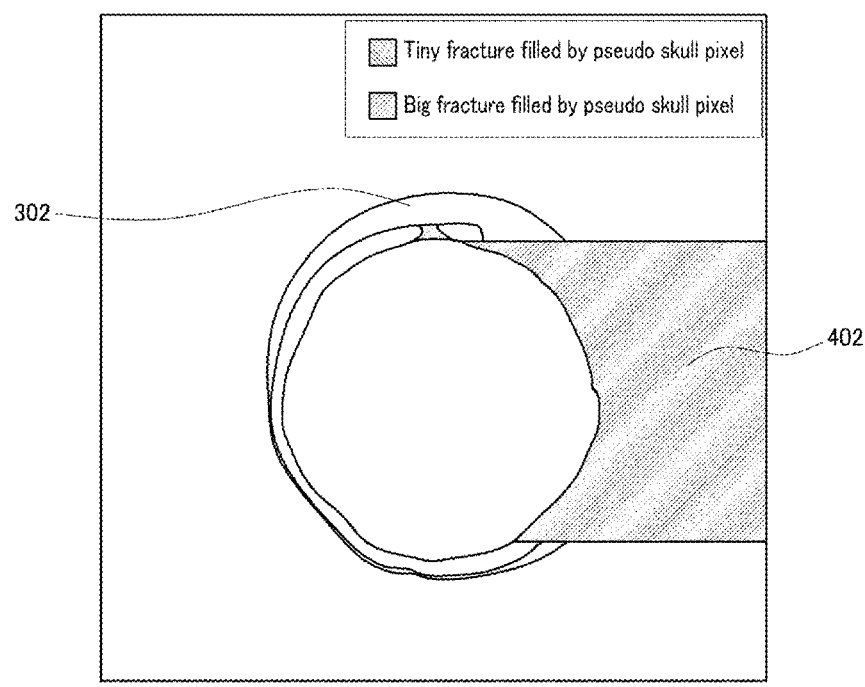
FIG. 16 illustrates a result of overlaying pixels of tiny and big fractures with pseudo skull pixels, in the method for eliminating an artifact of a computed tomography image in accordance with an example embodiment.

FIG. 16 illustrates a result of overlaying a tiny fracture with a pseudo skull pixel in the artifact elimination method for a computed tomography image in accordance with the example embodiment.

Meanwhile, in order to restore the most natural skull shape that would have been observed before the brain is opened, the artifact elimination method for a computed tomography image in accordance with the example embodiment may further include, after setting the starting point and the end point of the fracture, resetting and correcting the starting point and the end point of the fracture. In accordance with the example embodiment, once the starting point and the end point of the fraction are found, their coordinates may be moved to the skull pixel that is present on the opposite side from the fracture and has been stored prior to setting the axis of symmetry.

Figure 17:
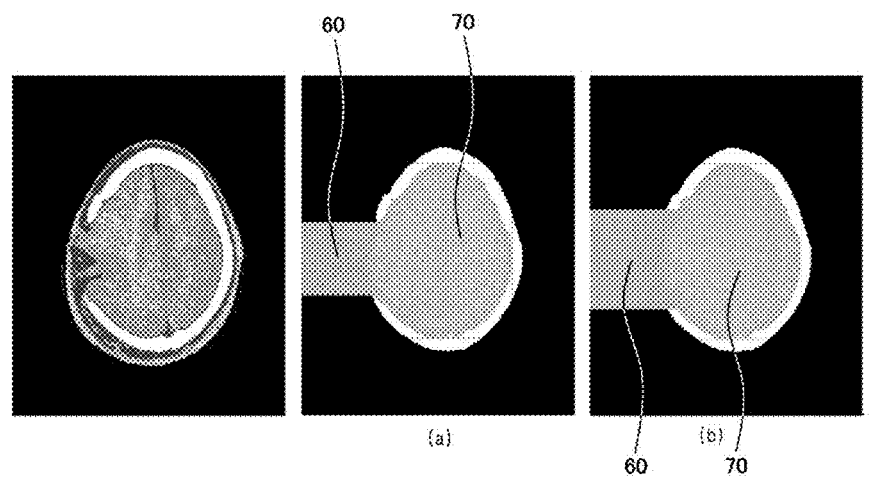
FIG. 17 shows comparison between a result of resetting a starting point and an end point of a big fracture and a result of not resetting them.

FIG. 17 provides diagrams showing a comparison between results of overlaying a big fracture with a pseudo skull pixel in each of cases where a starting point and an end point of a fracture are reset and not reset, respectively.

FIG. 17(a) shows a computed tomography image of a patient underwent craniotomy, in which a big fracture is overlaid with a pseudo skull pixel 60 by using an artifact elimination method without including the step of resetting a starting point and an end point of the fracture. FIG. 17(b) shows a result 70 of overlaying a big fracture with the pseudo skull pixel 60 by using the artifact elimination method that further includes the resetting of a starting point and an end point of a fracture, in the computed tomography image of a patient underwent craniotomy.

As illustrated in FIGS. 17(a) and 17(b), by resetting the starting point and the end point of the fracture, it is possible to obtain a more natural outcome, when the fracture of the brain is overlaid with a pseudo skull pixel.

Finally, returning to FIG. 1, the artifact elimination method for a computed tomography image in accordance with the example embodiment enables to collectively eliminate artifacts from a multiple number of computed tomography images and solely extract the brain tissues by eliminating pixel values except for skull pixels.

In general, since a computed tomography image desired to analyze includes a range from the cerebellum to the top of the head, it may be necessary to omit analyzing computed tomography images of the brain portion under the nasal cavity and the top of the head, when batch analysis is conducted. Since the brain portion under the nasal cavity and the top of the head are commonly characterized in that they have a far higher ratio of skull pixels than other brain portions, a ratio between brain tissue pixels and skull pixels is used to distinguish the top of the head and the portion under the nasal cavity in the example embodiment.

In the example embodiment, as a result of conducting a significant number of batch analyses for nineteen patients, the performance of distinguishing the brain portion under the nasal cavity is found to be the most effective when the ratio between the number of skull pixels and the number of brain tissue pixels is 0.7:1 or higher. This reference has resulted in omission of analysis of computed tomography images in the vicinity of the top of the head. Accordingly, it is efficient to approximately estimate the width and the length of the brain by using the boundary points of the brain, and, on this basis, differentiate the reference for the ratio between the number of skull pixels and the number of brain tissue pixels depending on the size of the brain.

For example, if the width and the length of the brain are less than 150 pixels, a reference for the ratio of the skull pixels to the brain tissue pixels may be 10:1, and if the width and the length of the brain are between 150 pixels and 250 pixels, the reference may be 5:1. In addition, if the width and the length of the brain are less than 100, the corresponding part may be regarded as the top of the head, and analysis thereof may be omitted.

Next, at step S500 of eliminating an artifact, pixels may be scanned inwardly from an edge of the computed tomography image. Subsequently, once a skull pixel is found, all the pixels that have been read so far are eliminated, and the scanning is continued for the next line or column. In this case, pixels may be read in all four directions, i.e., from a left top end point to a right bottom end point, from a left bottom end point to a right top end point, from a right top end point to a left top end point, and from a right bottom end point to a left top end point. In such cases, the algorithm for the method of eliminating an artifact is same in all cases except that the scanning directions are different.

Elimination of an artifact is based on the assumption that all brain tissues are enclosed by the skull. Thus, if any part of the brain tissues is not covered with the skull, there may be an error that all the brain tissues of the corresponding row or column are eliminated.

Figure 18:
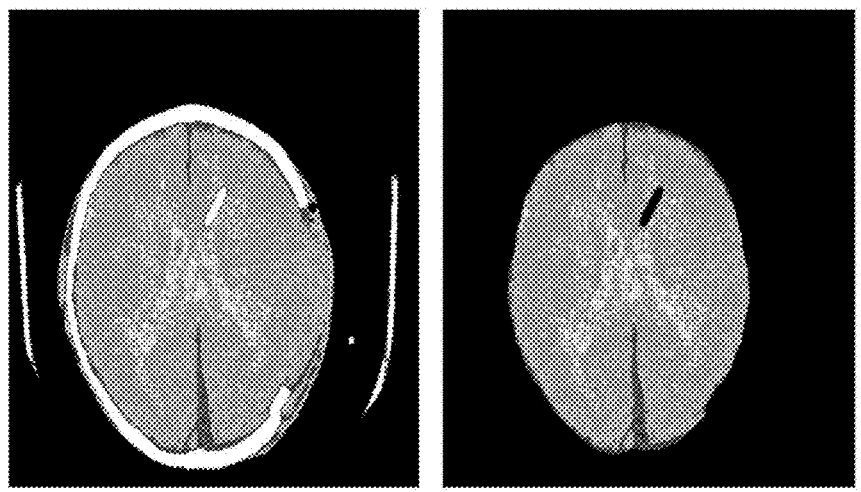
FIG. 18 shows a result of processing a computed tomography image by using an improved algorithm, when a starting point of a fracture is placed at a close position to that of a shunt or catheter.

FIG. 18 shows a result of processing a computed tomography image by using an improved algorithm, where a starting point of a fracture and a shunt or catheter are placed at close positions.

Meanwhile, an apparatus for eliminating an artifact of a computed tomography image by using the artifact elimination method according to the example embodiment may include a memory and a processing unit that is arranged to interface with the memory.

In addition, the apparatus for eliminating an artifact of a computed tomography image in accordance with an example embodiment may extract a distribution of HU values of the brain tissues from a computed tomography image of a patient, from which an artifact has been eliminated. Here, in case of the brain portion below the temporal bone, an artifact may not be easily eliminated due to the complicated bone structure, and, thus, computed tomography images in the range from the brain portion above the temporal bone to the top of the head, from which the brain tissue alone can be stably extracted, may be used for analysis.

On a computed tomography image, pixels of the major elements within the skull, i.e., the brain tissues, the cerebrospinal fluid, the blood, etc., have certain HU values ranging from 1 to 79. Accordingly, an attenuation threshold value may be limited to 0 to 79, and pixels without having HU values in the range from 0 to 79 may not be analyzed. A ratio of the certain pixels having the valid HU values in a computed tomography image may be obtained by using the following simple mathematical formula.

$$0 \leq \lambda \leq 79, \text{ and } \sum_{\lambda=0}^{79} p_\lambda = 100 \qquad \text{[Mathematical Formula 12]}$$

Here, $p_\lambda$ denotes a ratio of the pixels having the HU values in the range from 0 to 79 within a computed tomography image, and the corresponding ratio in the computed tomography image is a percentage ranging from 0 to 100. In addition, a sum of all $p_\lambda$ values becomes 100 according to the definition of $p_\lambda$.

For example, in case of a patient with traumatic brain injury, several computed tomography images are acquired in computer tomography examination. If n sheets of computed tomography images have been acquired, the number of pixels having $\lambda$ HU in a $k^{th}$ computed tomography image is denoted as $\lambda_c^k$. Accordingly, the number E of the pixels having the HU value of 0 to 79 in all of the computed tomography images may be represented by the following mathematical formula.

$$E = \sum_{k=1}^{n} \sum_{\lambda=0}^{79} \lambda_c^k \qquad \text{[Mathematical Formula 13]}$$

Accordingly, the ratio of the pixels having the HU value of 0 to 79 within a computed tomography image is represented as follows.

$$p_\lambda = \frac{1}{E} \sum_{k=1}^{n} \lambda_c^k \qquad \text{[Mathematical Formula 14]}$$

Here, n denotes the number of the acquired computed tomography images.

The distribution of the HU values of the brain tissues of the patient with brain injury may be acquired by calculating $p_\lambda$ for all $\lambda$. If there is a discrepancy in the distribution of HU values of certain pixels of the brain tissues of the patient with brain injury, it may mean a significant outcome indicating difference in the degree of the cerebral edema.

In addition, the artifact elimination method for a computed tomography image in accordance with the example embodiment may further include a color mapping process, after the automatic elimination of an artifact in the computed tomography image of the patient underwent craniotomy. Accordingly, it is possible to enable a user to more easily analyze a computed tomography image.

Figure 19:
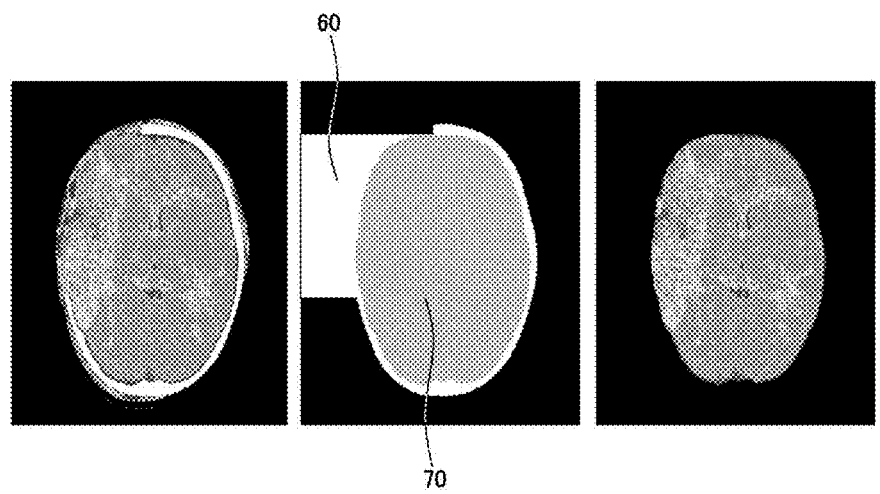
FIG. 19 shows a result of extracting brain tissues alone by using the method for eliminating an artifact of a computed tomography image in accordance with an example embodiment.

FIG. 19 shows a result of extracting brain tissues alone by using the artifact elimination method for a computed tomography image in accordance with the example embodiment.

The left image of FIG. 19 is a computed tomography image prior to conducting the elimination of an artifact; the middle image of FIG. 19 shows a process of overlaying a fracture present in a computed tomography image with a skull pixel in accordance with the example embodiment; and the right image of FIG. 19 shows a result of carrying out color mapping, after the automatic elimination of an artifact from a computed tomography image of a patient underwent craniotomy in accordance with the example embodiment. In the figure, a reference numeral 65 refers to the skull, and a reference numeral 75 denotes the brain tissues.

Subsequently, an artifact was eliminated, and a distribution of HU values of the brain tissues was extracted, based on the standardized computed tomography images.

Figure 20:
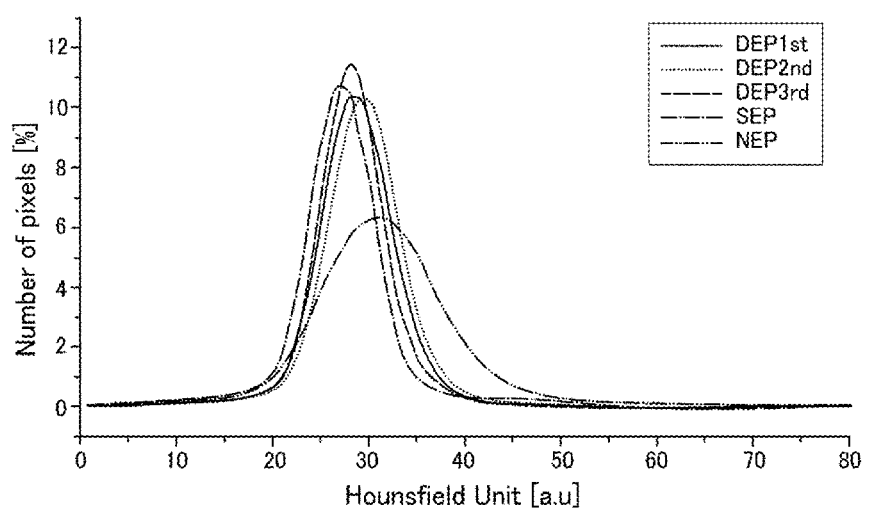
FIG. 20 is a graph showing a distribution of Hounsfield unit (HU) values, after artifacts are eliminated from computed tomography images of a patient with severe cerebral edema and a normal person by using the method for eliminating an artifact of a computed tomography image in accordance with an example embodiment.

FIG. 20 is a graph showing a distribution of HU values, after eliminating artifacts in computed tomography images of a patient suffering from severe cerebral edema (SEP) and a normal person (NEP) by using the method for eliminating an artifact of a computed tomography image in accordance with the example embodiment.

Additionally, FIG. 20 also provides analysis results for HU distributions of first (DEP1st), second (DEP2nd) and third (DEP3rd) computed tomography images of a patient who was diagnosed to have delayed cerebral edema.

As illustrated in FIG. 20, it is observed that HU distribution of a normal person and HU distribution of a patient with cerebral edema are different from each other, and the HU distribution of the first, second, and third computed tomography images of the patient with delayed cerebral edema is similar to HU distribution of a patient with severe cerebral edema. However, upon reviewing the radiology reports for the patient diagnosed to have the delayed cerebral edema, the patient was diagnosed to be normal in the report of the first computed tomography image, and then diagnosed to have the delayed cerebral edema in the analysis of the third computed tomography image conducted after the lapse of days. As in the aforementioned example, when observers analyze computed tomography images, the delayed cerebral edema may not be easily identified by naked eyes as it is widely distributed across the soft brain tissues, and exact diagnosis may not be made depending on abilities of the individual observers. As a resolution, by using the artifact elimination method for a computed tomography image in accordance with the example embodiment, it is possible to make an exact diagnosis when examining a patient with a brain injury whose prognosis is significantly affected by early detection.

The example embodiments can be embodied in a storage medium including instruction codes executable by a computer or processor such as a program module executed by the computer or processor. A computer readable medium can be any usable medium which can be accessed by the computer and includes all volatile/nonvolatile and removable/non-removable media. Further, the computer readable medium may include all computer storage and communication media. The computer storage medium includes all volatile/nonvolatile and removable/non-removable media embodied by a certain method or technology for storing information such as computer readable instruction code, a data structure, a program module or other data. The communication medium typically includes the computer readable instruction code, the data structure, the program module, or other data of a modulated data signal such as a carrier wave, or other transmission mechanism, and includes information transmission mediums.

The above-described apparatus for eliminating an artifact of a computed tomography image in accordance with the example embodiments may be realized as a computer readable code on a computer readable storage medium. The computer readable storage medium includes all kinds of storage devices storing data that can be read by a computer system. For example, there are a read only memory (ROM), a random access memory (RAM), a magnetic tape, a magnetic disk, a flash memory, an optical data storage device and others. In addition, the computer readable record medium may be distributed on a computer system connected through a computer communication network, to be stored and executed as a code that can be read in a distributed manner.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept

I claim:

1. A method for eliminating an artifact of a computed tomography image, comprising:

eliminating a machine artifact from a cross-sectional computed tomography image of the brain based on a positive HU (Hounsfield Unit) value in the computed tomography image;
setting boundary points positioned on a horizontal axis and a vertical axis in the computed tomography image, from which the machine artifact has been eliminated;
resetting a boundary point positioned at a boundary between the skull of the brain and the brain tissue by detecting a pixel sequence in a direction toward the center of the brain tissue;
detecting a position of a fracture of the brain in the computed tomography image, in which the boundary point has been reset, and overlaying a fracture region with an artificial skull pixel having the same HU value range as a skull pixel; and
eliminating an artifact from the computed tomography image, which has been overlaid with the skull pixel.

2. The method for eliminating an artifact of a computed tomography image as claimed in claim 1, wherein the eliminating of the machine artifact comprises:
detecting a pixel group having the positive HU value;
determining whether the pixel group having the positive HU value corresponds to the machine artifact; and
eliminating the machine artifact.

3. The method for eliminating an artifact of a computed tomography image as claimed in claim 2,
wherein the determining of whether or not to correspond to the machine artifact determines whether the pixel group having the positive HU value corresponds to the machine artifact, when the pixel group having the positive HU value is found, and then, a pixel group having a negative HU value is found.

4. The method for eliminating an artifact of a computed tomography image as claimed in claim 3,
wherein the pixel group having the negative HU value may be a void pixel group, and the number of the void pixels ranges from 25 to 35.

5. The method for eliminating an artifact of a computed tomography image as claimed in claim 1,
wherein the setting of the boundary points comprises setting a horizontal axis of the brain, where the horizontal axis is a line, in which the largest number of pixels having the positive HU value are present.

6. The method for eliminating an artifact of a computed tomography image as claimed in claim 1,
wherein the resetting of the boundary points comprises detecting a pixel sequence in a direction toward the center of the brain tissue, and
the pixel sequence includes one tissue pixel and a plurality of skull pixels.

7. The method for eliminating an artifact of a computed tomography image as claimed in claim 6,
wherein if the pixel sequence is not detected during the detecting of the pixel sequence,
a point moved from the initially set boundary point toward the center of the brain tissue by 25 to 30 pixels is reset as a boundary point of the brain.

8. The method for eliminating an artifact of a computed tomography image as claimed in claim 1,
wherein the overlaying of the fracture region with the skull pixel comprises classifying the fracture into a tiny fracture or a big fracture.

9. The method for eliminating an artifact of a computed tomography image as claimed in claim 8,
wherein the classifying of the fracture into a tiny fracture or a big fracture classifies a fracture, which is present in a direction parallel with an X or Y axis in a computed tomography image and has a length of 20 pixels or less, or a fracture, which is present in a direction having inclination of 1 or −1 and has a length of 15 pixels or less, is regarded as a tiny fracture, and
if a size of a fracture is larger than the above-described condition for the tiny fracture, the fracture is regarded as a big fracture.

10. The method for eliminating an artifact of a computed tomography image as claimed in claim 1, wherein the overlaying of the fracture region with the skull pixel comprises:
classifying the fracture into a tiny fracture or a big fracture;
overlaying the tiny fracture region with the skull pixel; and
overlaying the big fracture region with the skull pixel.

11. The method for eliminating an artifact of a computed tomography image as claimed in claim 10, wherein the overlaying of the big fracture region with the skull pixel comprises:
detecting a starting point and an end point of the big fracture; and
classifying the big fracture into airy one of right, left, upper and lower fractures, and once the starting point and the end point of the big fracture are detected, a fracture index is set to 1, and the detection of the big fracture is finished.

12. The method for eliminating an artifact of a computed tomography image as claimed in claim 10,
wherein the detecting of the starting point and the end point of the big fracture further comprises resetting the starting point and the end point of the big fracture based on the initial starting point and the end point of the big fracture,
wherein the resetting of the starting point and the end point of the big fracture moves coordinates of the initially set starting point and end point of the big fracture to the opposite skull pixel.

13. The method for eliminating an artifact of a computed tomography image as claimed in claim 1,
wherein the overlaying of the fracture region with the skull pixel symmetrizes the fracture region with the normal skull line on the opposite side to overlay the HU value of the fracture part with HU of the symmetrized normal skull pixels.

14. An apparatus for eliminating an artifact of a computed tomography image, comprising:
a storage device that stores an artifact elimination application; and
a processor configured to perform the artifact elimination application,
wherein according to execution of the artifact elimination application, the processor
eliminates a machine artifact from a cross-sectional computed tomography image of the brain based on a positive HU (Hounsfield Unit) value in the computed tomography image,
sets boundary points positioned on a horizontal axis and a vertical axis of the brain in the computed tomography image, from which the machine artifact has been eliminated,
resets a boundary point positioned at a boundary between the skull of the brain and the brain tissue by detecting a pixel sequence in a direction toward the center of the brain tissue, detects a position of a fracture of the brain in the computed tomography image, in which the boundary point has been reset, and overlaying the fracture region with an artificial skull pixel having the same HU value range as a skull pixel, and eliminating an artifact from the computed tomography image, which has been overlaid with the skull pixel.

15. The apparatus for eliminating an artifact of a computed tomography image of claim 14, wherein the processor detects a pixel group having the positive HU value, and determines whether the pixel group having the positive HU value corresponds to the machine artifact, and then, eliminates the machine artifact.

16. The apparatus for eliminating an artifact of a computed tomography image of claim 14, wherein the processor sets a horizontal axis of the brain, where the horizontal axis is a line, in which the largest number of pixels having the positive HU value are present.

17. The apparatus for eliminating an artifact of a computed tomography image of claim 14, wherein the processor of resetting the boundary points comprises detecting a pixel sequence in a direction toward the center of the brain tissue, and the pixel sequence includes one tissue pixel and a plurality of skull pixels.

18. The apparatus for eliminating an artifact of a computed tomography image of claim 14, wherein the processor of overlaying the region with the skull pixel symmetrizes the fracture region with the normal skull line on the opposite side to overlay the HU value of the fracture part with HU of the symmetrized normal skull pixels.

19. A non-transitory computer readable medium storing a program for executing the method for eliminating an artifact of a computed tomography image according to claim 1.

* * * * *